United States Patent [19]

Kagiya et al.

[11] Patent Number: 4,927,941

[45] Date of Patent: May 22, 1990

[54] FLUORINE-CONTAINING NITROAZOLE DERIVATIVES AND RADIOSENSITIZER COMPRISING THE SAME

[75] Inventors: Tsutomu Kagiya; Mitsuyuki Abe, both of Kyoto; Seiichi Nishimoto, Nara; Yuta Shibamoto, Kyoto; Kazuhiro Shimokawa, Settsu; Yorisato Hisanaga, Ibaraki; Tatsuo Nakada; Toru Yoshizawa, both of Osaka, all of Japan

[73] Assignee: Yasunori Nishijima & Daikin Industries Ltd., Kyoto, Japan

[21] Appl. No.: 204,367

[22] Filed: Jun. 9, 1988

[30] Foreign Application Priority Data

Jun. 10, 1987 [JP] Japan .................................. 62-147459
Jun. 24, 1987 [JP] Japan .................................. 62-156787
Sep. 26, 1987 [JP] Japan .................................. 62-241574
Dec. 10, 1987 [JP] Japan .................................. 62-314686
Jan. 29, 1988 [JP] Japan .................................. 63-20456
Mar. 31, 1988 [JP] Japan .................................. 63-79230

[51] Int. Cl.$^5$ ............................................ C07D 249/10
[52] U.S. Cl. .................................... 548/264.8; 546/210
[58] Field of Search ...................... 548/266; 546/210

[56] References Cited

FOREIGN PATENT DOCUMENTS 0000928 3/1979 European Pat. Off.
0095906 12/1983 European Pat. Off.
0212558 3/1987 European Pat. Off.

OTHER PUBLICATIONS

Shibamoto, et al, "Radiosensitization in Vitro, etc.", CA 105:186742h (1986).
Chemical Abstracts, vol. 107, No. 9 (1987), p. 73465t.
Chemical Abstracts, vol. 89, No. 23 (1978), p. 191005a.
Chemical Abstracts, vol. 89, Chem. Substance Index, I-Po, p. 2720CS.
Chemical Abstracts, vol. 89, No. 23 (1978), p. 191006b.
Chemical Abstracts, vol. 105, No. 18 (1986), p. 160447r.
Patent Abstracts of Japan, vol. 11, No. 18 (C-398) [2465], 17h Jan. 1987.
Patent Abstracts of Japan, vol. 9, No. 211 (C-300) [1934], 29th Aug. 1985.
Chemical Abstracts, vol. 105, No. 15 (1986), p. 130194p.
Int. J. Radiat. Biol., 19, 575–585, 1971.
Int. J. Radiat. Biol., 35, 151–160, 1979.

*Primary Examiner*—Richard L. Raymond
*Assistant Examiner*—Patricia L. Morris
*Attorney, Agent, or Firm*—Birch, Stewart, Kolasch & Birch

[57] ABSTRACT

A nitroazole derivative of the formula:

$$NA-R_f \qquad (I)$$

wherein NA is 3-nitro-1,2,4-triazol-1-yl and $R_f$ is a fluorine-containing organic group which is useful as a radiosensitizer.

1 Claim, No Drawings

FLUORINE-CONTAINING NITROAZOLE DERIVATIVES AND RADIOSENSITIZER COMPRISING THE SAME

BACKGROUND OF THE INVENTION

1. Field of the Invention

The present invention relates to novel fluorine-containing nitroazole derivatives and a radiosensitizer comprising the same, more particularly, a radiosensitizer comprising a specific fluorine-containing nitroazole derivatives such as 3-nitro-1,2,4-triazole or 2-nitroimidazole compound having a fluorine containing group at the 1-position, which facilitates inactivation of intractable hypoxic cells in malignant tumors by irradiation.

2. DESCRIPTION OF THE RELATED ART

To suppress reproduction or growth of malignant tumor cells, radiation exposure and administration of antitumor compounds or immunity substances are known and actually employed independently or in combination with surgical therapy. Among them, the radiation exposure has been employed for a long time.

A hypoxic cell sensitizer (or radiosensitizer) which is a drug for increasing sensitivity of the hypoxic cells against the radiation has been developed since it is promising means for increasing effects of radiotherapy.

Hitherto, various hypoxic cell sensitizers have been developed (cf. "Gan to Kagakuryoho" (Cancers and chemotherapy), Vol. 8, No. 11, Nov. 1981, 1659).

1-(2-Nitro-1-imidazolyl)-3-methoxy-2-propanol (Misonidazole), which is one of typical hypoxic cell sensitizers, is about twice as effective as when no Misonidazole is used. However, it is hardly administered in an effective amount since it has strong neurotoxicity. No sensitizing effect was confirmed from the results obtained by administering it in human beings (cf. Reference 4 cited in the above "Gan to Kagakuryoho").

To increase sensitizing activity of the radiation and simultaneously to decrease the neurotoxicity, nitrotriazole derivatives and nitroimidazole derivatives have been studied (cf. Japanese Patent Kikai Publication Nos. 194019/1986 and 12763/1987). However, the conventional derivatives have insufficient radiosensitization.

It has been found that the radiosensitizing function of the azole compounds is attributed to their azole rings while the side chain contributes to their solubility in oils and pharmacological characteristics (Int. J. Radiat. Biol., 35, 1979, 151).

Compounds having a fluorine atom at a specific position in a molecule have been increasingly used as medicines because of mimic effects of the fluorine atom or modification of metabolic inhibition effect and solbility in oils (cf. "Kagakuno Ryoiki" (Chemical Fields), 35, 441 (1981)).

SUMMARY OF THE INVENTION

One object of the present invention is to provide a novel fluorine-containing nitroazole derivatives such as a nitrotriazole or nitroimidazole derivative having a partially or completely fluorinated substituent on its azole ring.

Another object of the present invention is to provide a fluorine-containing radiosensitizer which increases sensitivity of the hypoxic cells against radiation but has improved pharmacological characteristics and low toxicity and neurotoxicity.

Accordingly, the present invention provides a nitroazole derivative of the formula:

$$NA-R_f \qquad (I)$$

wherein NA represents 3-nitro-1,2,4-triazol-1-yl of the formula:

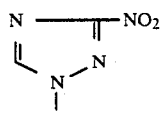
(II)

or 2-nitroimidazol-1-yl of the formula:

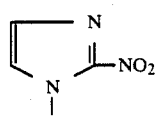
(III)

and $R_f$ is a fluorine-containing organic group provided that when NA is 2-nitroimidazol-1-yl, the fluorine-containing organic group has at least one fluorine atom on a carbon atom which bonds to the nitrogen atom of the imidazole ring or a carbon atom which bonds to said carbon atom and a radiosensitizer comprising said nitroazole derivative.

DETAILED DESCRIPTION OF THE INVENTION

Among the nitroazole derivative of the present invention, preferred is a nitroazole derivative (I) in which $R_f$ is a group of the formula:

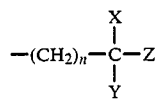
(IV)

wherein X is a hydrogen atom or a fluorine atom; Y is a fluorine atom, a chlorine atom, a trifluoromethyl group, a methyl group or a hydroxyl group, or X and Y together represent =O; Z is a hydrogen atom, a fluorine atom, a $C_1$-$C_5$ alkyl or fluoroalkyl group which may be substituted with hydroxyl, a group of the formula:

$$-(CHE)_m-CO-OR_1 \qquad (V)$$

wherein $R_1$ is a hydrogen atom or a $C_1$-$C_5$ alkyl or fluoroalkyl group, E is a hydrogen atom or a fluorine atom and m is 0 or 1, $$-CO-R_2 \qquad (VI)$$

wherein $R_2$ is a $C_1$-$C_5$ alkyl or fluoroalkyl group,

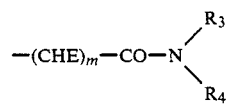
(VII)

wherein $R_3$ and $R_4$ are the same or different and a hydrogen atom, a hydroxyl group or a $C_1$-$C_5$ alkyl or fluoroalkyl group which may be substituted with a hydroxyl group, a $C_1$-$C_5$ alkoxy group or an amide group, or $R_3$ and $R_4$ forms a 3 to 6 membered ring together with the nitrogen atom to which they bond, and E and m are the same as defined above,

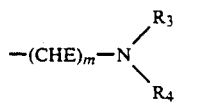         (VIII)-(1)

wherein $R_3$, $R_4$, E and m are the same as defined above,

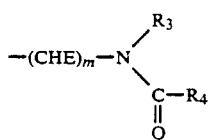         (VIII)-(2)

wherein $R_3$, $R_4$, E and m are the same as defined above,

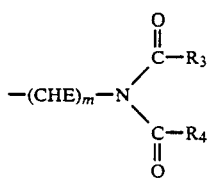         (VIII)-(3)

wherein $R_3$, $R_4$, E and m are the same as defined above,

—(CHE)$_m$—A—R$_5$         (IX)

wherein A is an oxygen atom or a sulfur atom, $R_5$ is a hydrogen atom, a $C_1$-$C_5$ alkyl or fluoroalkyl group which may be substituted with a hydroxyl group, a $C_1$-$C_5$ alkoxyl group or a $C_1$-$C_5$ oxyacyl group, a group of the formula: —CO—$R_6$ in which $R_6$ is a $C_1$-$C_5$ alkyl group,

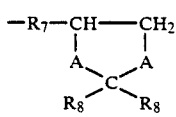         (X)

wherein $R_7$ is a $C_1$-$C_7$ alkylene group, $R_8$ is a $C_1$-$C_3$ alkyl group and A is the same as defined above, or

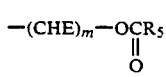         (XI)

wherein $R_5$ is a $C_1$-$C_5$ alkyl or fluoroalkyl group and E and m are the same as defined above. Y and Z may together form =CF—CF$_3$ or =CHOR$_6$ in which $R_6$ is the same as defined above. n is 0 or 1. However, $R_f$ is not —CH$_2$—CH$_2$F when NA is 2-nitroimidazol-1-yl.

—CH$_2$CF$_2$COOCH$_3$         (1)

—CH$_2$CF$_2$CONHCH$_2$CH$_2$OCH$_3$         (2)

—CH$_2$CF$_2$CONHCH$_2$CH$_2$OH         (3)

—CH(CH$_3$)—CH$_2$CONH(CH$_2$)$_2$OCH$_3$         (4)

—CH(CF$_3$)—CH$_2$COOCH$_3$         (5)

—CH$_2$CH(OH)CH$_2$OCH$_2$CF$_2$CF$_2$H         (6)

—CH$_2$CHFCH$_2$OCH$_3$         (7)

—CH$_2$CHFCH$_2$OCOCH$_3$         (8)

—CH$_2$CHFCH$_2$OH         (9)

—CH$_2$CH=CHOCH$_2$CF$_3$         (10)

—CF=CFCF$_3$         (11)

—CF$_2$CF$_2$H         (12)

—CH$_2$CH(OH)CH$_2$F         (13)

—CH$_2$CHFCONH(CH$_2$)$_2$OH         (14)

—CH$_2$CF$_3$         (15)

—CH$_2$CF$_2$COCH$_3$         (16)

—CH$_2$COCF$_3$         (17)

—CH$_2$COCHF$_2$         (18)

—CH$_2$COCH$_2$F         (19)

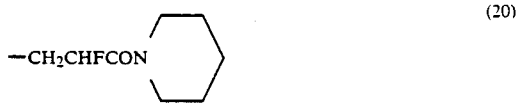         (20)

         (21)

         (22)

         (23)

         (24)

—CH$_2$CF$_2$CH$_2$OH         (25)

         (26)

—CH$_2$CF$_2$CH$_2$SCH$_3$         (27)

—CF$_2$CONH(CH$_2$)$_2$OH         (28)

         (29)

         (30)

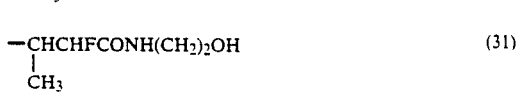         (31)

—CHClCHFCON (32)

—CHF$_2$ (33)

—CONH(CH$_2$)$_3$CF$_3$ (34)

—CH$_2$CH$_2$CHF$_2$ (35)

—CH$_2$F (36)

—CH$_2$CHFCOOCH$_3$ (37)

—CH$_2$CHFCONHCH$_2$CH$_2$OCH$_3$ (38)

—CH$_2$CF$_2$CH$_2$NH$_2$ (39)

—CH$_2$CF$_2$CH$_2$NHCOCH$_3$ (40)

—CH$_2$CF$_2$CH$_2$NHCOCH$_2$CH$_2$OH (41)

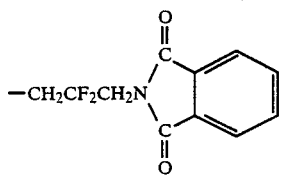 (42)

—CH$_2$CF$_2$CONH$_2$ (43)

—CH$_2$CF$_2$CONHOH (44)

—CH$_2$CF$_2$CONHCH$_2$CH$_2$NH$_3$Cl (45)

—CH$_2$CF$_2$CH$_2$NHCH$_2$CH$_2$OCH$_3$ (46)

—CH$_2$CHFCONHCH$_2$CH$_2$OH (47)

—CH$_2$CF$_2$CONHCH$_2$CH$_3$ (48)

—CH$_2$CF$_2$CONHCH$_2$CH$_2$CH$_3$ (49)

—CH$_2$CF$_2$CONH(CH$_2$)$_5$CH$_3$ (50)

—CH$_2$CF$_2$CONHCH$_2$CF$_3$ (51)

—CH$_2$CF$_2$CONH(CH$_2$)$_3$CF$_3$ (52)

—CH$_2$CF$_2$CONHCH(CH$_3$)$_2$ (53)

—CH$_2$CF$_2$CONHC(CH$_3$)$_2$ (54)

—CH$_2$CF$_2$CONHC (55)

—CH$_2$CF$_2$CONH(CH$_2$)$_2$OCH$_2$CH$_3$ (56)

—CH$_2$CF$_2$CONH(CH$_2$)$_3$OCH$_2$CH$_3$ (57)

—CH$_2$CF$_2$CONH(CH$_2$)$_3$OCH$_3$ (58)

—CH$_2$CF$_2$CONH(CH$_2$)$_3$OH (59)

—CH$_2$CF$_2$CONHCH$_2$CH(OH)CH$_3$ (60)

—CH$_2$CF$_2$CONH(CH$_2$)$_2$O(CH$_2$)$_2$OH (61)

—CH$_2$CF$_2$CONHCH$_2$CH$_2$CONH$_2$ (62)

—CH$_2$CHFCH$_2$OCH$_2$CH$_2$OCH$_3$ (63)

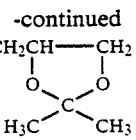 (64)

—CH$_2$CHFCH$_2$OCH$_2$CH(OH)CH$_2$OH (65)

—CH$_2$CHFCH$_2$OCH$^{CH_2OCOCH_3}_{CH_2OCOCH_3}$ (66)

—CH$_2$CHFCH$_2$OCH<$^{CH_2OH}_{CH_2OH}$ (67)

—CH$_2$CHFCH$_2$OCH$_2$CH$_2$OH (68)

The nitroazole derivative (I) of the present invention may be prepared as follows:

(A) When R$_f$ is a fluoroalkyl group:

(1) A fluorine-containing epoxy compound is addition reacted with 3-nitro-1,2,4-triazole or 2-nitroimidazole to form a fluoroalkyl group having a hydroxyl group as the group R$_f$.

The reaction temperature is from 0° to 100° C., preferably from 50° to 70° C. Although no solvent is required, the reaction may be carried out in a solvent such as alcohol, dioxane and the like.

(2) The hydroxyl group in the compound obtained in the above (1) is fluorinated with a suitable fluorinating agent (e.g. diethylaminosulfatrifluoride (DAST)).

The reaction is carried out in an aprotic solvent (e.g. methylene chloride, chloroform and ether) at a temperature of 0° to 50° C.

(3) A fluoroolefin is addition reacted with 3-nitro-1,2,4-triazole or 2-nitroimidazole.

This addition reaction is carried out in an aprotic solvent (e.g. acetonitrile and dimethylformamide) in the presence of a base at a temperature of 0° to 100° C.

(B) When R$_f$ is a fluoroester group:

(1) A fluorine-containing α,β-unsaturated carbonyl compound is addition reacted with 3-nitro-1,2,4-triazole or 2-nitroimidazole.

The reaction is carried out in an aprotic solvent (e.g. dioxane and tetrahydrofuran) in the presence of an acid or a base at a temperature of 30° to 120° C.

(2) A fluorooxetane is addition reacted with 3-nitro-1,2,4-triazole or 2-nitroimidazole.

The reaction is carried out in an alcohol (e.g. methanol and ethanol) at a temperature of 0° to 50° C.

(C) When R$_f$ is a fluorine-containing amide group:

The compound prepared in (B) is further reacted with an amine.

This reaction is carried out in the absence of a solvent at a temperature of 0° to 100° C.

(D) When R$_f$ is a fluorine-containing amine group:

(1) The compound prepared in (C) is reduced with a suitable reducing agent. Any reducing agent that does not reduce the nitro group can be used. For example, B$_2$H$_6$ is preferred. Any solvent that does not deactivate the reducing agent may be used. For example, tetrahydrofuan and dioxane are used.

(E) When R$_f$ is a fluorine-containing amide group:

(1) The compound prepared in (D) is reacted with carboxylic halide, carboxylic anhydride or lactone. A solvent is not necessarily required. When the carboxylic anhydride is used, a base catalyst such as pyridine or morpholine may be used.

Among the above preparation reactions, typical reactions are represented by following reaction schemes:

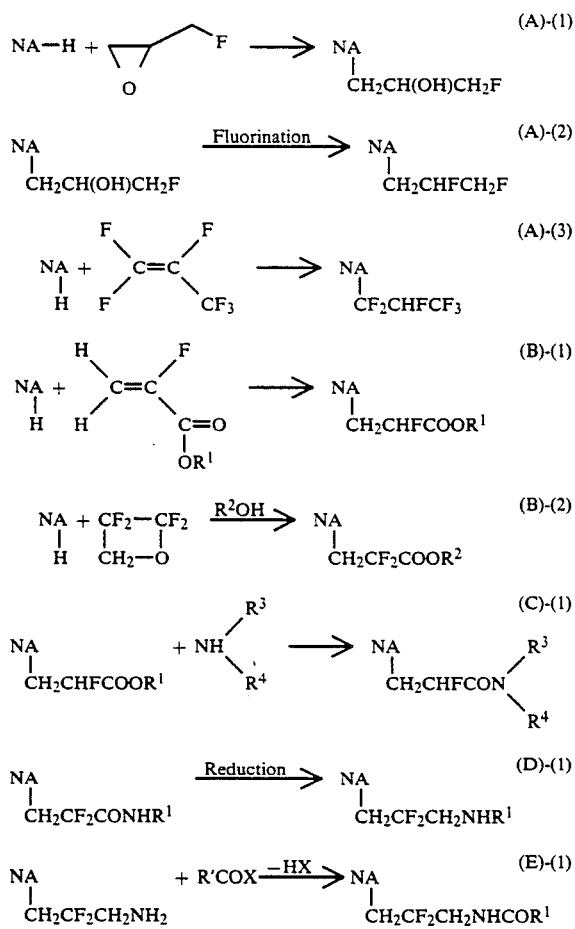

In the above formulas, $R^1$ and $R^2$ are independently a hydrogen atom or a lower alkyl group, X is a halogen atom, and NA is the same as defined above.

The nitroazole derivative (I) of the present invention is useful as a radiosensitizer. Its dose depends on the kinds of tumor and/or the compound (I). Generally, it is from 20 to 10,000 mg in case of oral administration, from 0.5 to 10,000 mg in case of injection or 20 to 10,000 mg in case of suppository. An optimum dose may be determined by a medical practitioner according to symptom based on a kind of radiation, a radiation dose, fractionation of irradiation and the like.

The nitroazole compound (I) of the present invention may be administered in any suitable form. The compound (I) may be compounded with any carrier which is conventionally used in this field, and formulated by a conventional method. The present invention is further illustrated by the following Preparation Examples for the nitroazole derivatives (I) and Examples showing the radiosensitization effect of the derivatives (I).

In Examples, "NT" means 3-nitro-1,2,4-triazol-1-yl and "NI" means 2-nitroimidazol-1-yl.

PREPARATION EXAMPLE 1

To 1.50 g (13.2 mmol) of 3-nitro-1,2,4-triazole and 3.00 g (28.3 mmol) of sodium carbonate, 30 ml of methanol was added. To the obtained mixture, 2.0 g (21 mmol) of tetrafluorooxetane was dropwise added with stirring at room temperature. After stirring for 30 minutes at room temperature, the reaction solution was concentrated and partitioned between ethyl acetate and water. The ethyl acetate phase was dried on magnesium sulfate and filtered. The filtrate was concentrated and subjected to isolation and purification by silica gel column chromatography to give 1.52 g of methyl 3-(3'-nitro-1',2',4'-triazol-1'-yl)-2,2-difluoropropionate.

m.p. 60.8°–62.5° C.

$^1$H-NMR (CDCl$_3$): $\delta$ = 3.98 (3H, s, —OCH$_3$), 4.97 (2H, t, —NCH$_2$, $J_{HF}$ = 13 Hz), 8.40 (1H, s, H$_5$).

$^{19}$F-NMR (standard: TFA): 30.8.

PREPARATION EXAMPLE 2

To a solution of 770 mg (3.26 mmol) of methyl 3-(3'-nitro-1',2',4'-triazol-1'-yl)-2,2-difluoropropionate in 5 ml of dioxane, 0.4 ml (4.6 mmol) of 2-methoxyethylamine was dropwise added and stirred for an hour at room temperature. Then, the reaction solution was concentrated and subjected to isolation and purification by silica gel column chromatography to give 570 mg of 3-(3'-nitro-1',2',4'-triazol-1'-yl)-2,2-difluoropropionic acid methoxyethylamide.

m.p. 66°–68° C.

$^1$H-NMR (CDCl$_3$): $\delta$ = 3.34 (3H, s, —CH$_3$), 3.30–3.58 (4H, m, —CH$_2$CH$_2$—O—), 5.00 (2H, t, H$_5$, $J_{HF}$ = 13 Hz), 6.91 (1H, bs, —CONH—), 8.38 (1H, s, H$_5$).

$^{19}$F-NMR (CDCl$_3$; standard: TFA): 31.3.

PREPARATION EXAMPLE 3

To a solution of 520 mg (2.20 mmol) of methyl 3-(3'-nitro-1',2',4'-triazol-1'-yl)-2,2-difluoropropionate in 4 ml of dioxane, 190 mg (3.1 mmol) of ethanolamine was added. After the same treatment as Preparation Example 2, 440 mg of 3-(3'-nitro-1',2',4'-triazol-1'-yl)-2,2-difluoropropionic acid hydroxyethylamide was obtained.

m.p. 118°–121.5° C.

$^1$H-NMR (DMSO-d$_6$): $\delta$ = 3.30–4.00 (4H, m, —CH$_2$CH$_2$—O—), 5.25 (2H, t, N$_1$—CH$_2$, $J_{HF}$ = 13 Hz), 8.16 (1H, bs, —CONH—), 8.83 (1H, s, H$_5$).

$^{19}$F-NMR (DMSO-d$_6$; standard: TFA): 33.5.

PREPARATION EXAMPLE 4

(a) Preparation of the compound corresponding to the formula:

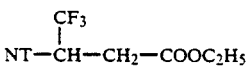

To a solution of 2.0 g (1.8 mmol) of 3-nitro-1,2,4-triazole in 10 ml of dioxane, 2.3 g (14 mmol) of ethyl trifluoromethylcrotonate was added. To the obtained solution, 3.0 g (23 mmol) of aluminum chloride was gradually added with keeping the temperature at 90° C. After the addition was completed, the reaction solution was heated to 100° C. for 4 hours.

After the reaction, the solution was concentrated and partitioned between chloroform and water. The chloroform phase was dried on magnesium sulfate and filtered. The filtrate was concentrated and subjected to isolation and purification by silica gel column chromatography to give 2.84 g of ethyl 3-(3'-nitro-1',2',4'-triazol-1'-yl)-4,4,4-trifluorobutyrate.

$^1$H-NMR (CDCl$_3$): $\delta$ = 1.26 (3H, t, —CH$_3$, $J_{H1''\text{-}H2''}$ = 7 Hz), 3.16 (1H, dd, H$_{2a}$, $J_{H2a\text{-}H2b}$ = 18 Hz, $J_{H1}$ = 3 Hz), 3.58 (1H, dd, H$_{2b}$, $J_{H1a\text{-}H2b}$ = 18 Hz, $J_{H1\text{-}H2b}$ = 11

Hz), 4.16 (2H, q, —OCH$_2$, J$_{H1''-H2''}$=7 Hz), 5.46 (1H, m, H$_{1'}$), 8.46 (1H, s, H$_5$).

$^{19}$F-NMR (CDCl$_3$; standard: TFA): −4.7.

(b) Preparation of the compound corresponding to the formula:

To 2.0 g (7.1 mmol) of ethyl 3-(3'-nitro-1',2',4'-triazol-1'-yl)-4,4,4-trifluorobutylate, 40 ml of 6N-HCl was added and reacted for 3 hours at 50° C. Then, the reaction solution was concentrated and dissolved in 20 ml of dioxane. Again, the solution was concentrated and dissolved in 10 ml of dioxane. To the solution, 2.0 ml (27 mmol) of thionyl chloride was dropwise added at room temperature. Then, the solution was heated at 70° C. for two hours.

The solution treated with thionyl chloride was dropwise added to a solution of 3.0 ml of 2-methoxyethylamine in 5.0 ml of dioxane with cooling by water and stirred for an hour at room temperature. Then, the reaction solution was concentrated and partitioned between chloroform and water. The chloroform phase was dried on magnesium sulfate and filtered. The filtrate was concentrated and subjected to isolation and purification by silica gel column chromatography to give 350 mg of 3-(3'-nitro-1',2',4'-triazol-1'-yl)-4,4,4-trifluorobutyric acid methoxyethylamide.

$^1$H-NMR (CDCl$_3$): δ=3.13 (1H, dd, H$_{2a}$, J$_{H1a-H2b}$=17 Hz, J$_{H2a-H1}$=3 Hz), 3.26 (3H, s, —OCH$_3$), 3.28–3.48 (3H, m, H$_{2b}$, H$_{2''}$), 3.55–3.75 (2H, m, H$_{1''}$), 5.68 (1H, m, H$_1$), 6.56 (1H, bs, —NH—), 8.51 (1H, s, H$_5$).

$^{19}$F-NMR (CDCl$_3$; standard: TFA): −4.8.

PREPARATION EXAMPLE 5

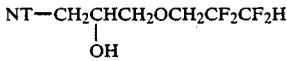

To 1.5 g (8.8 mmol) of 1-(2',3'-epoxypropyl)-3-nitro-1,2,4-triazole, 15 mmol of 2,2,3,3-tetrafluoropropanol and then 1.0 g (18 mmol) of potassium hydroxide were added and heated at 60° C. for 30 minutes. After the reaction, the solution was concentrated and partitioned between methylene chloride and water. The methylene chloride phase was washed with water, dried on magnesium sulfate and filtered. The filtrate was concentrated and subjected to isolation and purification by silica gel column chromatography to give 1.0 g of 1-(2'-hydroxy-3'-tetrafluoropropoxypropyl)-3-nitro-1,2,4-triazole.

$^1$H-NMR (CDCl$_3$): δ=3.60–3.82 (3H, m, H$_{3'}$, —OH), 3.75–4.13 (2H, m, —OCH$_2$CH$_2$—), 4.23–4.60 (3H, m, H$_{1'}$, H$_{2'}$), 5.96 (1H, tt, —CF$_2$H, J$_{F3''-F3'}$=53 Hz, J$_{F2-F3''}$=4 Hz), 8.36 (1H, s, H$_5$).

$^{19}$F-NMR (CDCl$_3$; standard: TFA): 59.6, 45.4.

PREPARATION EXAMPLE 6

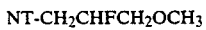

To a solution of 2.0 g (12 mmol) of 1-(2',3'-epoxypropyl)-3-nitro-1,2,4-triazole in methanol, 1.0 g (18 mmol) of potassium hydroxide was added and stirred for an hour at room temperature and then heated at 50° C. for 30 minutes. After the reaction, the mixture was filtered and the filtrate was concentrated and subjected to isolation and purification by silica gel column chromatography to give 1.1 g of 1-(2'-hydroxy-3'-methoxypropyl)-3-nitro-1,2,4-triazole. The product was dissolved in 10 ml of dry tetrahydrofuran (THF). To the solution, 1.5 g (9.3 mmol) of diethylaminosulfur trifluoride (DAST) was dropwise added with cooling by ice and then stirred for 5 hours at room temperature. After the reaction, 2.0 ml of water was added to the reaction solution to remove excess DAST. The solution was concentrated and subjected to isolation and purification by silica gel column chromatography to give 420 mg of 1-(2'-fluoro-3'-methoxypropyl)-3-nitro-1,2,4-triazole.

$^1$H-NMR (CDCl$_3$): δ=3.48 (3H, s, —OCH$_3$), 3.58 (2H, dd, H$_{3'}$, J$_{H2'-H3'}$=4 Hz, J$_{H3-F}$=6 Hz), 4.08–4.42 (2H, m, H$_{1'}$), 5.15 (1H, dm, —CHF—, J$_{H3'-F}$=47 Hz), 8.32 (1H, s, H$_5$).

$^{19}$F-NMR (CDCl$_3$; standard: TFA): 113.0.

PREPARATION EXAMPLE 7

To 4.2 g (25 mmol) of 1-(2',3'-epoxypropyl)-3-nitro-1,2,4-triazole, 50 ml of glacial acetic acid was added and reacted for 12 hours at 70° C. Then, the reaction solution was concentrated and subjected to isolation and purification by silica gel column chromatography to give 1.89 g (8.21 mmol) of 1-(3'-acetoxy-2'-hydroxypropyl)-3-nitro-1,2,4-triazole. The product was completely dissolved in 10 ml of dry tetrahydrofuran. To the solution, 2.0 g (12.4 mmol) of DAST was dropwise added with cooling by ice and then stirred overnight at room temperature. After the reaction, 2.0 ml of water was added to the reaction solution to remove excess DAST. The solution was concentrated and subjected to isolation and purification by silica gel column chromatography to give 463 mg of 1-(2'-fluoro-3'-acetoxypropyl)-3-nitro-1,2,4-triazole.

$^1$H-NMR (CDCl$_3$): δ=2.15 (3H, s, —COCH$_3$), 4.28–4.88 (4H, m, H$_{1'}$, H$_{3'}$), 5.12 (1H, dm, H$_{2'}$, J$_F$=46.6 Hz), 8.32 (1H, s, H$_5$).

$^{19}$F-NMR (CDCl$_3$; standard: TFA): 113.1.

PREPARATION EXAMPLE 8

2N-HCl was added to 420 mg (1.81 mmol) of 1-(2'fluoro-3'-acetoxypropyl)-3-nitro-1,2,4-triazole and stirred overnight at room temperature. Then, the reaction solution was concentrated and subjected to isolation and purification by silica gel column chromatography to give 230 mg of 1-(2'-fluoro-3'-hydroxypropyl)-3-nitro-1,2,4-triazole.

$^1$H-NMR (CDCl$_3$): δ=3.58–4.15 (2H, m, H$_{1'}$, H$_{3'}$), 4.44–4.68 (1H, m, H$_{1a'}$), 4.72–4.85 (1H, m, H$_{1b}$), 5.02 (1H, dm, H$_{2'}$, J$_{H2'-F}$=4.82 Hz), 8.30 (1H, s, H$_5$).

$^{19}$F-NMR (CDCl$_3$; standard: TFA): 115.4.

PREPARATION EXAMPLE 9

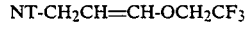

To a mixture of 1.9 ml (27 mmol) of 2,2,2-trifluoroethanol and 5.0 ml of dioxane, 1.0 g (18 mmol) of potassium hydroxide was added. To the obtained solution, a solution of 1.5 g (8.8 mmol) of 1-(2', 3'-epoxypropyl)-3-nitro-1,2,4-triazole in 5.0 ml of dioxane was dropwise added over about 10 minutes with stirring at 60° C. After the addition was completed, the reaction mixture was further reacted with heating for 20 minutes. Then, the reaction solution was concentrated and partitioned between methylene chloride and water. The methylene chloride phase was washed with water, dried on magnesium sulfate and filtered. The filtrate was concentrated and subjected to isolation and purification by silica gel column chromatography to give 420 mg of 1-[3'-(2'', 2'', 2''-trifluoroethoxy)-2', 3'-propenyl]-3-nitro-1,2,4-triazole as a mixture of cis and trans forms.

Cis form:
$^1$H-NMR (CDCl$_3$): δ=4.28–4.56 (2H, m, H$_{1'}$), 4.73 (2H, q, H$_{1''}$, $J_{H1''-CF3}$=9 Hz), 5.68 (1H, dt, H$_{2'}$, $J_{H2'-H3'}$=9Hz, $J_{H1'-H3'}$=6 Hz), 6.74 (1H, dt, H$_{3'}$, $J_{H1'-H3'}$=9 Hz $J_{H1'-H3'}$=6 Hz), 7.92 (1H, s, H$_5$).
$^{19}$F-NMR (CDCl$_3$; standard: TFA): −4.6.

Trans form:
$^1$H-NMR (CDCl$_3$): δ=4.28–4.56 (2H, m, H$_{1'}$), 4.73 (2H, q, H$_{1''}$, $J_{CF3}$=9 Hz), 6.42 (1H, dt, H$_{3'}$, $J_{H2}$=14 Hz, $J_{H1'}$=5 Hz), 7.00 (1H, dt, H$_{2'}$, $J_{H2'-H2'}$=14 Hz, $J_{H2'-H1''}$=2 Hz), 7.92 (1H, s, H$_5$).
$^{19}$F-NMR (CDCl$_3$; standard: TFA): −4.5.

PREPARATION EXAMPLE 10

NT-CF=CF-CF$_3$ 3.0 g (26 mmol) of 3-nitro-1,2,4-triazole and 7.0 g (66 mmol) of sodium carbonate were dissolved in 75 ml of dimethylformamide and stirred overnight at room temperature under hexafluoropropene atmosphere. Then, the reaction solution was concentrated and partitioned between chloroform and water. The chloroform phase was dried on magnesium sulfate and filtered. The filtrate was concentrated and subjected to isolation and purification by silica gel column chromatography to give 153 mg of 1-(1', 2', 3', 3', 3'-pentafluoropropenyl)-3-nitro-1,2,4-triazole as a mixture of cis and trans forms and 670 mg of 1-(1', 2', 3', 3', 3'-pentafluoropropyl)-3-nitro-1,2,4-triazole.

1-(1', 2', 3', 3', 3'-Pentafluoropropenyl)-3-nitro-1,2,4-triazole in cis form:
$^1$H-NMR (CDCl$_3$): δ=8.58 (1H, s, H$_5$).
$^{19}$F-NMR (CDCl$_3$; standard: TFA): 67.0, 20.6, 11.2.

1-(1', 2', 3', 3', 3'-Pentafluoropropenyl)-3-nitro-1,2,4-triazole in trans form:
$^1$H-NMR (CDCl$_3$): δ=8.69 (1H, s, H$_5$).
$^{19}$F-NMR (CDCl$_3$; standard: TFA): 85.2, 48.2, 10.9.

1-(1', 2', 3', 3', 3'-Pentafluoropropyl)-3-nitro-1,2,4-triazole:
$^1$H-NMR (CDCl$_3$): δ=5.31–6.10 (1H, m, H$_{2'}$), 8.74 (1H, d, H$_5$)
$^{19}$F-NMR (CDCl$_3$; standard: TFA): 131.7, 23.9, 7.5, −4.7.

PREPARATION EXAMPLE 11

NT-CF$_2$CF$_2$H 1.0 g (8.8 mmol) of 3-nitro-1,2,4-triazole and 2.0 g (19 mmol) of sodium carbonate were dissolved in 25 ml of dimethylformamide and heated at 100° C. for 5 hours under tetrafluoroethylene atmosphere. Then, the reaction solution was concentrated and partitioned between chloroform and water. The chloroform phase was dried on magnesium sulfate and filtered. The filtrate was concentrated and subjected to isolation and purification by silica gel column chromatography to give 318 mg of 1-(1', 2', 2', 2'-tetrafluoroethyl)-3-nitro-1,2,4-triazole.

$^1$H-NMR (CDCl$_3$): δ=6.54 (1H, tt, H$_{2'}$, $J_{H2'-F2'}$=52 Hz, $J_{H2-F1'}$=4 Hz).
$^{19}$F-NMR (CDCl$_3$; standard: TFA): 58.5, 22.5.

PREPARATION EXAMPLE 12

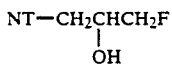
NT—CH$_2$CHCH$_2$F
         |
         OH

To a solution of 1.11 g (6.52 mmol) of 1-(2', 3'-epoxypropyl)-3-nitro-1,2,4-triazole in 10 ml of dioxane, 2.0 g of pyridine hydrofluoride (Oler reagent) was added with stirring at room temperature and stirred for one hour. 2.0 g of calcium carbonate was added to the reaction solution and the precipitate formed was filtered off. The filtrate was concentrated and subjected to purification by silica gel column chromatography (eluent: chloroform/methanol) to give 340 mg of 1-(3'-fluoro-2'-hydroxypropyl)-3-nitro-1,2,4-triazole.

$^1$H-NMR (CDCl$_3$): δ=4.36–4.70 (3H, m, H$_{1'}$, H$_{1'}$), 4.51 (2H, dm, H$_{3'}$, $J_{H3'-F}$=47 Hz), 8.34 (1H, s, H$_5$).
$^{19}$F-NMR (CDCl$_3$; standard: TFA): 153.4.

PREPARATION EXAMPLE 13

NT-CH$_2$CF$_2$CH$_2$OH          (25)

To a solution of 2.0 g (9.0 mmol) of 3-(3'-nitro-1', 2', 4'-triazol-1'-yl)-2,2-difluoropropionic acid in 30 ml of THF, 1.00 g (26.4 mmol) of NaBH$_4$ was gradually added at −70° C. under nitrogen atmosphere. To the obtained solution, a solution of 2.5 ml (20.2 mmol) of BF$_3$O(C$_2$H$_5$)$_2$ in 10 ml of THF was dropwise added with cooling and reacted for an hour with stirring.

Then, 25 ml of ethanol was added to the resulting solution with cooling by iced/water to deactivate the excess reducing agent. The solvent was distilled off and the residue was partitioned between ethyl acetate/saturated aqueous sodium chloride solution. The ethyl acetate phase was dried on magnesium sulfate and filtered. The filtrate was concentrated and subjected to isolation and purification by silica gel column chromatography to give 550 mg of 1-(2', 2'-difluorohydroxypropyl)-3-nitro-1,2,4-triazole.

$^1$H-NMR (CDCl$_3$): δ=2.97 (1H, t, —OH, J=6.5 Hz), 3.89 (2H, dt, H$_{3'}$, $J_{H3'-OH}$=6.5 Hz, $J_{H3-F}$=13 Hz), 4.84 (2H, t, H$_{1'}$, $J_{H3'-F}$=13 Hz), 8.36 (1H, s, H$_5$).
$^{19}$F-NMR (CDCl$_3$; standard: TFA): 33.0.

PREPARATION EXAMPLE 14

NT-CH$_2$CHFCONHCH$_2$CH$_2$OCH$_3$          (38)

To a solution of 510 mg of methyl 3-(3'-nitro-1', 2', 4'-triazol-1'-yl)-2-fluoropropionate in 20 ml of dioxane, 830 mg of methoxyethylamine was added and stirred for 5 hours at room temperature. Then, the reaction solution was concentrated under vacuum and subjected to purification by silica gel column chromatography to give 390 mg of 3-(3'-nitro-1', 2', 4'-triazol-1'-yl)-2-fluoropropionic acid methoxyethylamide.

$^1$H-NMR (DMSO-d$_6$): δ=5.10 (2H, dd, H$_1$, $J_{H1'-H2'}$=4 Hz, $J_{H1'-F}$=24 Hz), 5.56 (1H, d, t, H$_{2'}$, $J_{H1'-H2'}$=4 Hz, $J_{HF}$=48 Hz), 8.75 (1H, s).
$^{19}$F-NMR (DMSO-d$_6$; standard: TFA): 116.7.

PREPARATION EXAMPLE 15

NT-CH$_2$CF$_2$CH$_2$NHCOCH$_3$   (40)

To a solution of 1.21 g of 3-(3'-nitro-1', 2', 4'-triazol-1'-yl)-2,2-difluoropropylamine in 50 ml of THF, 1.0 g of acetic anhydride and 1.0 g of pyridine were added and stirred for two hours at room temperature. After the reaction, THF was distilled off under vacuum and the residue was subjected to purification by silica gel column chromatography to give 720 mg of 3-(3'-nitro-1', 2', 4'-triazol-1'-yl)-2,2-difluoropropyl-acetamide.
m.p. 126.5°–128.2° C.
$^1$H-NMR: $\delta$=2.08 (3H, s), 3.88 (2H, dt, H$_{3'}$, $J_{H-F}$=16 Hz, $J_{H3'-NH}$=6 Hz), 5.16 (2H, t, $J_{HF}$=16 Hz), 8.60 (1H, t, H$_{NH}$, $J_{HNH-H3'}$=6 Hz), 9.12 (1H, s).
$^{19}$F-NMR (DMSO-d$_6$; standard: TFA): 28.5.

PREPARATION EXAMPLE 16

NT-CH$_2$CF$_2$CH$_2$NHCOCH$_2$CH$_2$OH   (41)

To a solution of 1.04 g of 3-(3'-nitro-1', 2', 4'-triazol-1'-yl)-2,2-difluoropropylamine in 50 ml of THF, 1.37 g of β-propiolactone was added and reacted for two hours at room temperature. Then, the solvent was distilled off. The residue was dissolved in 200 ml of ethyl acetate, washed with water, dried on anhydrous magnesium sulfate and filtered. The filtrate was concentrated and subjected to purification by silica gel column chromatography to give 280 mg of 3-(3'-nitro-1', 2', 4'-triazol-1'-yl)-2,2-difluoropropyl-(2''-hydroxypropion)-amide.
m.p. 102.0°–104.0° C.
$^1$H-NMR (DMSO-d$_6$): $\delta$=2.54 (2H, t, H$_{1''}$, $J_{H1''-H2''}$=7 Hz), 3.60–4.00 (4H, m), 5.50 (2H, t, $J_{H-F}$=16 Hz), 8.52 (1H, t, H$_{NH}$, $J_{HNH-H3'}$=6 Hz), 9.00 (1H, s).
$^{19}$F-NMR (DMSO-d$_6$; standard: TFA): 28.1.

PREPARATION EXAMPLE 17

NT-CH$_2$CF$_2$CONH$_2$   (43)

To a solution of 20.0 g (80 mmol) of methyl 3-(3'-nitro-1', 2', 4'-triazol-1'-yl)-2,2-difluoropropionate in 100 ml of methanol, 200 ml of 10% ammonia-methanol solution was dropwise added and then stirred for 3 hours at room temperature. Then, a colorless crystalline precipitated by cooling was recrystallized from methanol to give 16.6 g of 3-(3'-nitro-1', 2', 4'-triazol-1'-yl)-2,2-difluoropropionamide.
m.p. 146.0°–147.5° C.
$^1$H-NMR (DMSO-d$_6$): $\delta$=5.24 (2H, t, $J_{H-F}$=16 Hz), 8.25 (1H, br, s), 8.44 (1H, br, s), 9.00 (1H, s).
$^{19}$F-NMR (DMSO-d$_6$; standard: TFA): 30.8.

PREPARATION EXAMPLE 18

NT-CH$_2$CF$_2$CH$_2$NH$_2$   (39)

To a solution of 8.8 g (39.8 mmol) of 3-(3'-nitro-1', 2', 4'-triazol-1'-yl)-2,2-difluoropropionamide in 100 ml of dry THF, 4.52 g (119 mmol) of sodium borohydride was slowly added with cooling by ice under nitrogen atmosphere. To the obtained suspension, a solution of 16.1 ml of BF$_3$-ether complex in 50 ml of THF was slowly added with cooling by ice and then stirred for 4 hours with cooling by ice and for 4 hours at room temperature. Then, the reaction solution was poured into water, acidified by the addition of dilute hydrochloric acid and stirred for two hours. Then, the solution was alkalized by the addition of an aqueous potassium hydroxide solution and extracted with ethyl acetate.

The extract was dried on magnesium sulfate and filtered. The filtrate was concentrated and subjected to purification by silica gel column chromatography to give 980 mg of 3-(3'-nitro-1', 2', 4'-triazol-1'-yl)-2,2-difluoropropylamine.
$^1$H-NMR (DMSO-d$_6$): $\delta$=3.08 (2H, t, $J_{HF}$=15 Hz), 5.06 (2H, t, $J_{HF}$=15 Hz), 8.97 (1H, s).
$^{19}$F-NMR (DMSO-d$_6$; standard: TFA): 30.3.

PREPARATION EXAMPLE 19

NT-CH$_2$CF$_2$CONHOH   (44)

To a solution of 1.88 g of methyl 3-(3'-nitro-1', 2', 4'-triazol-1'-yl)-2,2-difluoropropionate in 50 ml of methanol, 1.4 g of hydroxyamine hydrochloride was added. To the obtained solution, a solution of 0.4 g of potassium hydroxide in 50 ml of methanol was slowly added.

After the reaction, the solution was concentrated and then dissolved in 100 ml of ethyl acetate, washed with water (50 ml ×2), dried on anhydrous magnesium sulfate and filtered. The filtrate was concentrated and subjected to purification by silica gel column chromatography to give 0.7 g of 3-(3'-nitro-1', 2', 4'-triazol-1'-yl)-2,2-difluoropropionic acid hydroxyamide.
$^1$H-NMR (deuterated acetone): $\delta$=3.32 (1H, s), 5.28 (2H, t, $J_{H-F}$=15 Hz), 8.73 (1H, s).
$^{19}$F-NMR (deuterated acetone): 33.4.

PREPARATION EXAMPLE 20

NT—CH$_2$CF$_2$CONHCH$_2$CH$_2$$\overset{+}{N}$H$_3$$\overset{-}{C}$l   (45)

To a solution of 5.00 g of methyl 3-(3'-nitro-1', 2', 4'-triazol-1'-yl)-2,2-difluoropropionate in 30 ml of THF, 5.0 g of ethylenediamine was added and reacted for 2 hours at room temperature. Then, the solution was concentrated under vacuum. To the concentrate, hydrochloric acid was added to give 3.2 g of 3-(3'-nitro-1', 2', 4'-triazol-1'-yl)-2,2-difluoropropionamidoethylammonium chloride.
$^1$H-NMR (DMSO-d$_6$): $\delta$=3.40–3.58 (4H, m), 5.34 (2H, t, $J_{H-F}$=16 Hz), 9.13 (1H, s).
$^{19}$F-NMR (DMSO-d$_6$; standard: TFA): 31.4.

PREPARATION EXAMPLE 21

NT-CH$_2$CF$_2$CH$_2$NHCH$_2$CH$_2$OCH$_3$   (46)

A solution of 1.25 g (5 mmol) of 3-(3'-nitro-1', 2', 4'-triazol-1'-yl)-2,2-difluoropropionic acid methoxyethylamide in 50 ml of dry diglyme was cooled by ice under nitrogen atmosphere. To the solution, 0.38 g (10 mmol) of NaBH$_4$ was added and then, with cooling by ice, a solution of 1.8 ml (13.5 mmol) of BF$_3$-ether complex in 30 ml of diglyme was slowly dropwise added. Then, the solution was stirred for 2 hours with cooling by ice and then for 4 hours at room temperature. The reaction solution was slowly poured into dilute hydrochloric acid and then alkalized by the addition of an aqueous sodium hydroxide solution. Then, the solution was extracted with ethyl acetate.

The extract was dried on magnesium sulfate and filtered. The filtrate was concentrated and subjected to purification by silica gel column chromatography to give 0.11 g of 3-(3'-nitro-1', 2', 4'-triazol-1'-yl)-2,2-difluoropropyl-methoxyethylamine.

$^1$H-NMR (DMSO-d$_6$): δ=2.81 (2H, t, H$_A$, J$_{HAHB}$=5 Hz), 3.12 (2H, t, J$_{HF}$=15 Hz), 3.30 (3H, s), 3.42 (2H, t, H$_B$, J$_{HAHB}$=5 Hz), 5.08 (2H, t, J$_{H-F}$=15 Hz), 9.00 (1H, s).

$^{19}$F-NMR (DMSO-d$_6$; standard: TFA): 27.8.

PREPARATION EXAMPLE 22

NT-CH$_2$CHFCONHCH$_2$CH$_2$OH  (47)

To a solution of 510 mg of methyl 3-(3'-nitro-1', 2', 4'-triazol-1'-yl)-2-fluoropropionate in 20 ml of dioxane, 830 mg of hydroxyethylamide was added and stirred for 5 hours at room temperature. Then, the reaction solution was concentrated under vacuum. The concentrate was subjected to purification by silica gel column chromatography to give 310 mg of 3-(3'-nitro-1', 2', 4'-triazol-1'-yl)-2-fluoropropionic acid hydroxyethylamide.

$^1$H-NMR (DMSO-d$_6$): δ=5.10 (2H, dd, H$_A$, J$_{HA-HB}$=4 Hz, J$_{H-F}$=24 Hz), 5.60 (1H, d, t, H$_B$, J$_{HA-HB}$=4 Hz, J$_{H-F}$=48 Hz), 8.80 (1H, s).

$^{19}$F-NMR (DMSO-d$_6$; standard: TFA): −116.0.

PREPARATION EXAMPLE 23

NT-CH$_2$CF$_2$CONHCH$_2$CH$_3$  (48)

To a solution of 2.36 g of methyl 3-(3'-nitro-1', 2', 4'-triazol-1'-yl)-2,2-difluoropropionate in 50 ml of dioxane, 1 ml of ethylamine (70%) was added.

After the reaction, the solution was concentrated and subjected to purification by silica gel column chromatography to give 1.78 g of 3-(3'-nitro-1', 2', 4'-triazol-1'-yl)-2,2-difluoropropionic acid ethylamide.

m.p. 69.3°–71.0° C.

$^1$H-NMR (DMSO-d$_6$; standard: TMS): δ=1.17 (3H, t, J$_{H1''-H2''}$=8 Hz), 3.31 (2H, quint, J$_{H1''-H2''}$=6 Hz), 5.36 (2H, t, J$_{HF}$=15 Hz), 9.12 (2H, m).

$^{19}$F-NMR (DMSO-d$_6$; standard: TFA): 31.3 (t, J$_{HF}$=15 Hz).

PREPARATION EXAMPLE 24

NT-CH$_2$CF$_2$CONHCH$_2$CH$_2$CH$_3$  (49)

To a solution of 2.36 g of methyl 3-(3'-nitro-1', 2', 4'-triazol-1'-yl)-2,2-difluoropropionate in 50 ml of dioxane, 0.65 g of propylamine was added.

After the reaction, the solution was concentrated and subjected to purification by silica gel column chromatography to give 1.50 g of 3-(3'-nitro-1', 2', 4'-triazol-1'-yl)-2,2-difluoropropionic acid n-propylamide.

m.p. 66.0°–68.7° C.

$^1$H-NMR (DMSO-d$_6$; standard: TMS): δ=0.94 (3H, t, J$_{H1''-H2''}$=6 Hz), 1.53 (2H, sext, J$_{H1''-H2''}$=J$_{H2''-H3''}$=J$_{H2''-NH}$=6 Hz), 3.24 (2H, q, J$_{H2''-H3''}$=J$_{H2''-NH}$=6 Hz), 5.37 (2H, t, J$_{HF}$=15 Hz), 9.12 (2H, m).

$^{19}$F-NMR (DMSO-d$_6$; standard: TFA): 30.9 (t, J$_{HF}$=15 Hz).

PREPARATION EXAMPLE 25

NT-CH$_2$CF$_2$CONH(CH$_2$)$_5$CH$_3$  (50)

To a solution of 2.36 g of methyl 3-(3'-nitro-1', 2', 4'-triazol-1'-yl)-2,2-difluoropropionate in 50 ml of dioxane, 1.8 g of n-hexylamine was added.

After the reaction, the solution was concentrated and subjected to purification by silica gel column chromatography to give 2.1 g of 3-(3'-nitro-1', 2', 4'-triazol-1'-yl)-2,2-difluoropropionic acid hexylamide.

m.p. 73.6°–75.8° C.

$^1$H-NMR (DMSO-d$_6$; standard: TMS): δ=0.96 (3H, t, J$_{H1''-H2''}$=6 Hz), 1.10–1.70 (8H, m), 3.24 (2H, q, J$_{H2''-H3''}$=7 Hz), 5.33 (2H, t, J$_{HF}$=15 Hz), 9.10 (2H, m).

$^{19}$F-NMR (DMSO-d$_6$; standard: TFA): 30.8 (t, J$_{HF}$=15 Hz).

PREPARATION EXAMPLE 26

NT-CH$_2$CF$_2$CONHCH$_2$CF$_3$  (51)

To a solution of 2.36 g of methyl 3-(3'-nitro-1', 2', 4'-triazol-1'-yl)-2,2-difluoropropionate in 50 ml of dioxane, 2.0 g of trifluoroethylamine hydrochloride was added and then 1.5 g of triethylamine was slowly dropwise added with vigorously stirring.

The solvent was distilled off and the residue was dissolved in 200 ml of ethyl acetate and washed with water. The ethyl acetate solution was dried on magnesium sulfate, concentrated and subjected to purification by silica gel column chromatography to give 1.6 g of 3-(3'-nitro-1', 2', 4'-triazol-1'-yl)-2,2-difluoropropionic acid trifluoroethylamide.

m.p. 103.5°–105.5° C.

$^1$H-NMR (DMSO-d$_6$; standard: TMS): δ=4.08 (2H, m), 5.40 (2H, t, J$_{HF}$=15 Hz), 9.90 (1H, s), 9.84 (1H, t, J$_{H1''-HNH}$=6 Hz).

$^{19}$F-NMR (DMSO-d$_6$; standard: TFA): −8.1 (3F, t, J$_{HF}$=10 Hz), 30.7 (2F, t, J$_{HF}$=14 Hz).

PREPARATION EXAMPLE 27

NT-CH$_2$CF$_2$CONH(CH$_2$)$_3$CF$_3$  (52)

To a solution of 2.36 g of methyl 3-(3'-nitro-1', 2', 4'-triazol-1'-yl)-2,2-difluoropropionate in 50 ml of dioxane, 2.5 g of trifluorobutylamine hydrochloride was added and then 1.5 g of triethylamine was slowly dropwise added with vigorously stirring.

Then, the solvent was distilled off and the residue was dissolved in 200 ml of ethyl acetate and washed with water. The ethyl acetate solution was dried on magnesium sulfate, concentrated and subjected to purification by silica gel column chromatography to give 1.8 g of 3-(3'-nitro-1', 2', 4'-triazol-1'-yl)-2,2-difluoropropionic acid trifluorobuthylamide.

m.p. 58.3°–61.5° C.

$^1$H-NMR (DMSO-d$_6$; standard: TMS): δ=1.40–2.60 (4H, m), 3.23 (2H, q, J$_{H1''-H2''}$=7 Hz), 5.28 (2H, t, J$_{HF}$=15 Hz), 9.02 (1H, s), 9.12 (1H, t, J$_{H5''-H1''}$=5 Hz).

$^{19}$F-NMR (DMSO-d$_6$; standard: TFA): −13.5 (3F, t, J$_{HF}$=12 Hz), 31.0 (2F, t, J$_{HF}$=15 Hz).

PREPARATION EXAMPLE 28

NT-CH$_2$CF$_2$CONHCH(CH$_3$)$_2$  (53)

To a solution of 2.36 g of methyl 3-(3'-nitro-1', 2', 4'-triazol-1'-yl)-2,2-difluoropropionate in 50 ml of dioxane, 0.65 g of isopropylamine was added.

Then, the reaction solution was concentrated and subjected to purification by silica gel column chromatography to give 2.24 g of 3-(3'-nitro-1', 2', 4'-triazol-1'-yl)-2,2-difluoropropionic acid isopropylamide.

m.p. 83.8°–86.1° C.

$^1$H-NMR (DMSO-d$_6$; standard: TMS): δ=1.20 (6H, d, J$_{H1''-H2''}$=6 Hz), 4.08 (1H, m), 5.36 (2H, t, J$_{HF}$=15 Hz), 8.94 (1H, d, J$_{H2''-H4''}$=8 Hz), 9.12 (1H, s).

$^{19}$F-NMR (DMSO-d$_6$; standard: TFA): 31.0 (t, J$_{HF}$=15 Hz).

PREPARATION EXAMPLE 29

NT-CH$_2$CF$_2$CONH-C(CH$_3$)$_3$  (54)

To a solution of 2.22 g of 3-(3'-nitro-1', 2', 4'-triazol-1'-yl)-2,2-difluoropropionic acid in dioxane, 2.00 g of thionyl chloride was added and reacted for 2 hours at room temperature. Then, 5 ml of tert.-butylamine was added and further reacted.

The reaction solution was dissolved in 200 ml of ethyl acetate and washed with water. The ethyl acetate solution was dried on magnesium sulfate, concentrated and subjected to purification by silica gel column chromatography to give 1.2 g of 3-(3'-nitro-1', 2', 4'-triazol-1'-yl)-2,2-difluoropropionic acid tert.-butylamide.
m.p. 60.5°–63.0° C.

$^1$H-NMR (DMSO-d$_6$; standard: TMS): δ=1.40 (9H, s), 5.30 (2H, t, J$_{HF}$=14 Hz), 8.36 (br, s, NH), 9.07 (1H, s).

$^{19}$F-NMR (DMSO-d$_6$; standard: TFA): 30.1 (t, J$_{HF}$=14 Hz).

PREPARATION EXAMPLE 30

NT—CH$_2$CF$_2$CONHC⟨▷  (55)

To a solution of 2.36 g of methyl 3-(3'-nitro-1', 2', 4'-triazol-1'-yl)-2,2-difluoropropionate in 50 ml of dioxane, 0.85 g of cyclopropylamine was added.

After the reaction, the solution was concentrated and subjected to purification by silica gel column chromatography to give 2.04 g of 3-(3'-nitro-1', 2', 4'-triazol-1'-yl)-2,2-difluoropropionic acid cyclopropylamide.
m.p. 114.6°–116.6° C.

$^1$H-NMR (DMSO-d$_6$; standard: TMS): δ=0.50–1.00 (4H, m), 2.90 (1H, m), 5.36 (2H, t, J$_{HF}$=15 Hz), 9.13 (1H, s).

$^{19}$F-NMR (DMSO-d$_6$; standard: TFA): 30.9 (t, J$_{HF}$=15 Hz).

PREPARATION EXAMPLE 31

NT-CH$_2$CF$_2$CONH(CH$_2$)$_2$OCH$_2$CH$_3$  (56)

To a solution of 2.36 g of methyl 3-(3'-nitro-1', 2', 4'-triazol-1'-yl)-2,2-difluoropropionate in 50 ml of dioxane, 1.6 g of ethanolamine ethyl ether was added.

After the reaction, the solution was concentrated and subjected to purification by silica gel column chromatography to give 3.1 g of 3-(3'-nitro-1', 2', 4'-triazol-1'-yl)-2,2-difluoropropionic acid ethanolamide ethyl ether.
m.p. 70.0°–71.5° C.

$^1$H-NMR (DMSO-d$_6$; standard: TMS): δ=1.19 (3H, t, J$_{H1''-H2''}$=8 Hz), 3.22–3.70 (6H, m), 5.32 (2H, t, J$_{HF}$=14 Hz), 9.08 (1H, s), 9.12 (1H, t, J$_{H2''-H5''}$=6 Hz).

$^{19}$F-NMR (DMSO-d$_6$; standard: TFA): 31.0 (t, J$_{HF}$=14 Hz).

PREPARATION EXAMPLE 32

NT-CH$_2$CF$_2$CONH(CH$_2$)$_3$OCH$_2$CH$_3$  (57)

To a solution of 2.36 g of methyl 3-(3'-nitro-1', 2', 4'-triazol-1'-yl)-2,2-difluoropropionate in 50 ml of dioxane, 2.0 g of propanolamine ethyl ether was added.

After the reaction, the solution was concentrated and subjected to purification by silica gel column chromatography to give 2.56 g of 3-(3'-nitro-1', 2', 4'-triazol-1'-yl)-2,2-difluoropropionic acid propanolamide ethyl ether.

$^1$H-NMR (DMSO-d$_6$; standard: TMS): δ=1.10 (3H, t, J$_{H1'''-H3'''}$=6 Hz), 1.68 (2H, quint, J$_{H2''-H3''}$=7 Hz), 3.10–3.60 (6H, m), 9.00 (1H, s), 5.36 (2H, t, J$_{HF}$=15 Hz).

$^{19}$F-NMR (DMSO-d$_6$; standard: TFA): 31.1 (t, J$_{HF}$=15 Hz).

PREPARATION EXAMPLE 33

NT-CH$_2$CF$_2$CONH(CH$_2$)$_3$OCH$_3$  (58)

To a solution of 2.36 g of methyl 3-(3'-nitro-1', 2', 4'-triazol-1'-yl)-2,2-difluoropropionate in 50 ml of dioxane, 1.34 g of propanolamine methyl ether was added.

After the reaction, the solution was concentrated and subjected to purification by silica gel column chromatography to give 2.97 g of 3-(3'-nitro-1', 2', 4'-triazol-1'-yl)-2,2-difluoropropionic acid propanolamide methyl ether.

$^1$H-NMR (DMSO-d$_6$; standard: TMS): δ=1.80 (2H, t, J$_{H1''-H2''}$=7 Hz), 3.20–3.60 (7H, m), 5.36 (2H, t, J$_{HF}$=15 Hz), 9.08 (2H, m).

$^{19}$F-NMR (DMSO-d$_6$; standard: TFA): 31.2 (t, J$_{HF}$=15 Hz).

PREPARATION EXAMPLE 34

NT-CH$_2$CF$_2$CONH(CH$_2$)$_3$OH  (59)

To a solution of 2.36 g of methyl 3-(3'-nitro-1', 2', 4'-triazol-1'-yl)-2,2-difluoropropionate in 50 ml of dioxane, 1.8 g of the propanolamine was added.

After the reaction, the solution was concentrated and subjected to purification by silica gel column chromatography to give 1.9 g of 3-(3'-nitro-1', 2', 4'-triazol-1'-yl)-2,2-difluoropropionic acid propanolamide.
m.p. 97.0°–99.6° C.

$^1$H-NMR (DMSO-d$_6$; standard: TMS): δ=1.60 (2H, m), 3.00–3.60 (4H, m), 4.50 (1H, s), 5.24 (2H, t, J$_{HF}$=15 Hz), 9.00 (1H, s).

$^{19}$F-NMR (DMSO-d$_6$; standard: TFA): 30.9 (t, J$_{HF}$=15 Hz).

PREPARATION EXAMPLE 35

NT—CH$_2$CF$_2$CONHCH$_2$CHCH$_3$  
       |  
       OH  (60)

To a solution of 2.36 g of methyl 3-(3'-nitro-1', 2', 4'-triazol-1'-yl)-2,2-difluoropropionate in 50 ml of dioxane, 1.8 g of isopropanolamine was added.

After the reaction, the solution was concentrated and subjected to purification by silica gel column chromatography to give 1.82 g of 3-(3'-nitro-1', 2', 4'-triazol-1'-yl)-2,2-difluoropropionic acid isopropanolamide.
m.p. 110.0°–112.8° C.

$^1$H-NMR (DMSO-d$_6$; standard: TMS): δ=1.08 (3H, d, J$_{H1''-H2''}$=6 Hz), 3.19 (2H, t, J$_{H1''-NH}$=6 Hz), 3.80 (1H, m), 4.84 (1H, d, J$_{H2''-OH}$=6 Hz), 5.34 (2H, t, J$_{HF}$=14 Hz), 9.08 (2H, m).

$^{19}$F-NMR (DMSO-d$_6$; standard: TFA): 30.9 (t, J$_{HF}$=14 Hz).

PREPARATION EXAMPLE 36

NT-CH$_2$CF$_2$CONH(CH$_2$)$_2$O(CH$_2$)$_2$OH  (61)

To a solution of 2.36 g of methyl 3-(3'-nitro-1', 2', 4'-triazol-1'-yl)-2,2-difluoropropionate in 50 ml of dioxane, 1.56 g of diglycolamine was added.

After the reaction, the solution was concentrated and subjected to purification by silica gel column chromatography to give 2.06 g of 3-(3'-nitro-1', 2', 4'-triazol-1'-yl)-2,2-difluoropropionic acid diglycolamide.

m.p. 74.5°–77.0° C.

$^1$H-NMR (DMSO-$d_6$; standard: TMS): δ=3.30–3.70 (8H, m), 5.36 (2H, t, $J_{HF}$=15 Hz), 4.70 (1H, s), 9.09 (2H, m).

$^{19}$F-NMR (DMSO-$d_6$; standard: TFA): 31.0 (t, $J_{HF}$=15 Hz).

EXAMPLE 1

Radiosensitization effect on cells (ER in vitro)

To examine the in vitro radiosensitization effect of the present nitroazole derivative (I), 100,000 cells of Chinese hamster V-79 cells were cultured in monolayer in a culture dish, and the V-79 cells in a log phase were prepared.

A solution of a predetermined concentration of a compound to be examined in a medium was added to the dish. After standing for 60 minutes at 37° C., the dish was placed in a closed vessel at room temperature. Then, the vessel was purged with nitrogen for 10 minutes to exclude oxygen and X-ray was irradiated at a dose rate of 1.6 Gy/min.

After the irradiation, the cells were washed with phosphate buffer and digested with trypsin into single cells. Then, a predetermined amount of the cells was introduced into 5 ml of a culture medium in a culture dish and cultured for 7 days at 37° C. After staining and washing with water, the number of colonies formed was counted.

The results are shown in following Table 1 as ER in vitro.

EXAMPLE 2

Radiosensitization effect on tumor transplanted in animal (ER in vivo)

To both thighs of male Balb/c mouse (8 weeks; 4 mice in a group), $10^5$ of EMT-6 tumor cells were subcutaneously inoculated. After the diameter of the tumor reached about 1 cm, a solution of a compound to be examined in saline was intraperitonealy administered (200 mg/kg). After 40 minutes from the administration, X-ray was irradiated at a dose rate of 450 rad/min. for 5 minutes and then the mouse was sacrificed.

After the mouse was systemically sterilized, the tumor was taken out and the tissue was homogenated. Then, 22 ml of trypsin was added to the homogenate and stirred for 50 minutes at 37° C. The number of cells in the supernatant was counted. A predetermined amount of the cells was introduced in a plastic plate having a diameter of about 5 cm. To the plate, 5 ml of medium was added and cultured in a $CO_2$ incubator. The plates containing the irradiated and unirradiated cells were removed from the incubator after 9 days and 10 days incubation, respectively. The cells were fixed by methanol and stained by Giemsa stain. Then, the number of colonies formed were counted.

The survival rate was calculated with using the unirradiated cells as control. The results are shown as ER in vivo in following Table 1.

TABLE 1

| Compound | $R_f$(NT-$R_f$) | ER in vitro (mM) | ER in vivo (mg/kg) | $LD_{50}$ (g/kg) |
|---|---|---|---|---|
| (1) | —$CH_2CF_2COOCH_3$ | 1.28 (1.0) | 1.0 (100) 1.0 (200) | — |
| (2) | —$CH_2CF_2CONH(CH_2)_2OCH_3$ | 1.78 (1.0) | 1.49 (50) 1.57 (200) | >3.0 |
| (3) | —$CH_2CF_2CONH(CH_2)_2OH$ | 1.55 (1.0) | 1.26 (100) 1.10 (200) | 1.6 |
| (4) | —CHCH$_2$CONH(CH$_2$)$_2$OCH$_3$ \| CF$_3$ | 1.62 (1.0) | 1.2 (100) | — |
| (6) | —CH$_2$CHCH$_2$OCH$_2$(CF$_2$)$_2$H \| OH | 1.49 (0.5) | 1.10 (50) 1.0 (200) | — |
| (7) | —$CH_2CHFCH_2OCH_3$ | 1.73 (1.0) | 1.42 (200) | >2.0 |
| (8) | —$CH_2CHFCH_2OCOCH_3$ | 1.97 (1.0) | 1.36 (100) 1.67 (200) | — |
| (9) | —$CH_2CHFCH_2OH$ | 1.64 (1.0) | 1.48 (100) | — |
| (10) | —$CH_2CH=CHOCH_2CF_3$ | 1.20 (0.5) | 1.05 (100) | — |
| (11) | —$CF=CFCF_3$ | 1.50 (1.0) | 1.0 (100) | — |
| (12) | —$CF_2CF_2H$ | 1.93 (1.0) | 1.10 (100) | — |
| (13) | —$CH_2CH(OH)CH_2F$ | 1.73 (1.0) | 1.37 (50) 1.45 (80) | 0.7 |
| Comp. (1) | —$CH_2CH(OH)CH_2Cl$ | 1.85 (1.0) | 1.2 (80) 1.45 (200) | >1.0 |
| Comp. (2) | —$CH_2CH(OH)CH_2Br$ | 1.67 (1.0) | — 1.39 (200) | >1.0 |
| Comp. (3) | —$CH_2CONHCH_2CH_2OCH_3$ | 1.43 (1.0) | 1.48 (200) | 2.73 |
| Comp. (4) | —$CH_2CH(OH)CH_2OCH_3$ (Misonidazole) | 1.62 (1.0) | 1.40 (100) 1.58 (200) | 1.5 |

TABLE 2

| Compound | $R_f$(NT-$R_f$) | ER in vivo (mg/kg) | $LD_{50}$ (g/kg) |
|---|---|---|---|
| (25) | —$CH_2CF_2CH_2OH$ | 1.55 (400) | |

TABLE 2-continued

| Compound | $R_f$(NT-$R_f$) | ER in vivo (mg/kg) | LD$_{50}$ (g/kg) |
|---|---|---|---|
| | | 1.57 (200) | |
| | | 1.48 (100) | |
| (38) | —CH$_2$CHFCONH(CH$_2$)$_2$OCH$_3$ | 1.18 (200) | |
| | | 1.19 (100) | |
| (39) | —CH$_2$CF$_2$CH$_2$NH$_2$ | 1.28 (200) | |
| (40) | —CH$_2$CF$_2$CH$_2$NHCOCH$_3$ | 1.46 (200) | |
| (41) | —CH$_2$CF$_2$CH$_2$NHCO(CH$_2$)$_2$OH | 1.43 (200) | |
| (43) | —CH$_2$CF$_2$CONH$_2$ | 1.62 (200) | 0.7 |
| (46) | —CH$_2$CF$_2$CH$_2$NHCH$_2$CH$_2$OCH$_3$ | 1.20 (200) | |
| (47) | —CH$_2$CHFCONH(CH$_2$)$_2$OH | 1.25 (200) | |
| | | 1.35 (100) | |
| (53) | —CH$_2$CF$_2$CONHCH(CH$_3$)$_2$ | 1.05 (200) | 0.6 |
| (60) | —CH$_2$CF$_2$CONHCH$_2$CH(OH)CH$_3$ | 1.43 (100) | 1.2 |
| (62) | —CH$_2$CF$_2$CONH(CH$_2$)$_2$CONH$_2$ | 1.43 (100) | 1.5 |
| (63) | —CH$_2$CHFCH$_2$OCH$_2$CH$_2$OCH$_3$ | 1.34 (100) | |
| (64) | —CH$_2$CHFCH$_2$OCH$_2$CH——CH$_2$<br>　　　　　　　　　　　　O＼＿／O<br>　　　　　　　　　　　　　　C<br>　　　　　　　　　　　　　(CH$_3$)$_2$ | 1.42 (100) | |
| (65) | —CH$_2$CHFCH$_2$OCH$_2$CH(OH)CH$_2$OH | 1.47 (100) | 1.6 |

The effects of the present compound (13) and the comparative compounds (1) and (2), all of which are nitrotriazole derivatives wherein R=—CH$_2$CH(OH)—CH$_2$Q, are compared. The ER in vivo of the compound (13), wherein Q=F, in a low concentration is comparable to that of the comparative compound (1) wherein Q=Br or the comparative compound (2) wherein Q=Cl.

In comparison of the compound (13) and (2), both of which are fluoride derivatives, it is shown that the compound (2) has a higher activity [ER=1.49 (50 mg/kg)] and a lower toxicity [LD$_{50}$>3.0 g/kg] than the compound (13).

As mentioned above, the activity and the toxicity of the compound are particularly improved by fluorination.

PREPARATION EXAMPLE 37

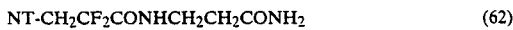

NT-CH$_2$CF$_2$CONHCH$_2$CH$_2$CONH$_2$　(62)

To a solution of 2.00 g (8.17 mmol) of methyl 1-(3'-nitro-1',2',4'-triazol-1'-yl)-2,2-difluoropropionate in 20 ml of dioxane, 1.50 g (10.7 mmol) of β-alanine methyl ester hydrochloride and 2.00 g (35.6 mmol) of potassium hydroxide were added and stirred for 30 minutes at room temperature.

After removing insoluble phase by decantation, the reaction solution was concentrated and partitioned between ethyl acetate and water. The ethyl acetate phase was dried on magnesium sulfate, filtered and concentrated to give 2.20 g of 1-(3'-nitro-1',2',4'-triazol-1'-yl)-2,2-difluoropropionic acid 3-alanine methyl ester (A).

To 1.80 g (5.86 mmol) of the compound (A), 20 ml of saturated solution of ammonia in methanol was added and reacted for 3 days at room temperature with stirring. After the reaction, the solution was concentrated and subjected to isolation and purification by silica gel column chromatography to give 437 mg of 1-(3'-nitro-1',2',4'-triazol-1'-yl)-2,2-difluoropropionic acid 3-alanylamide.

$^1$H-NMR (DMSO-d$_6$): δ=2.40 (2H, t, —CH$_2$CO—, J=7 Hz), 3.30–3.58 (2H, m, —NHCH$_2$—), 5.32 (2H, t, —CH$_2$CF$_2$—, J=15 Hz), 7.00 (1H, bs, —CONH$_2$), 7.50 (1H, bs, —CONH$_2$), 9.09 (1H, s, H$_5$), 9.14 (1H, t, —CONH—, J=6 Hz).

$^{19}$F-NMR (DMSO-d$_6$; standard: TFA): 31.1.

PREPARATION EXAMPLE 38

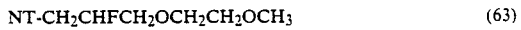

NT-CH$_2$CHFCH$_2$OCH$_2$CH$_2$OCH$_3$　(63)

To 25 g (0.27 mmol) of epichlorohydrin, 20.8 g (0.27 mmol) of methylcellosolve and 0.1 ml of conc. sulfuric acid were added and reacted for 10 hours at 100° C. After the reaction, 500 ml of ether was added and washed with saturated sodium hydrogen carbonate solution and with saturated sodium chloride solution. The ether phase was dried on magnesium sulfate, filtered and concentrated to give 20 g of 1-chloro-2-hydroxy-3-(2'-methoxyethoxy)propane. $^1$H-NMR (CDCl$_3$): δ=3.40 (3H, s, —OCH$_3$), 3.45–3.82 (9H, m, H$_1$, H$_3$, H$_{1'}$, H$_{2'}$, —OH), 3.84–4.18 (1H, m, H$_2$).

To a solution of 18 g (0.11 mol) of 1-chloro-2-hydroxy-3-(2'-methoxyethoxy)-propane in 300 ml of dioxane, 6.2 g (0.11 mol) of potassium hydroxide was added and reacted for 2 hours at 70° C. After the reaction, the reaction mixture was filtered and the filtrate was concentrated to give 6 g of 3-(2'-ethoxymethoxy)-1,2-epoxypropane.

$^1$H-NMR (CDCl$_3$): δ=2.60 (1H, dd, H$_{1a}$, J$_{H1b}$=7 Hz, J$_{H2}$=4 Hz), 2.82 (1H, dd, H$_{1b}$, J$_{H1a}$=7 Hz, J$_{H2}$=5 Hz), 3.06–3.30 (1H, m, H$_2$), 3.40 (3H, m, —OCH$_3$), 3.46–4.00 (6H, m, H$_3$, H$_{1'}$, H$_{2'}$).

To 2.0 g (15 mmol) of 3-(2'-ethoxymethoxy)-1,2-epoxypropane, 2.0 g (18 mmol) of 3-nitro-1,2,4-triazole and reacted for 3 hours at 90° C. After the reaction, 50 ml of ethyl acetate was added to the reaction mixture and washed with saturated sodium chloride solution. The ethyl acetate phase was dried on magnesium sulfate and filtered. The filtrate was concentrated and subjected to isolation and purification by silica gel column chromatography to give 1.8 g of 1-[2'-hydroxy-3'-(2''-methoxyethoxy)-propyl]-3-nitro-1,2,4-triazole.

$^1$H-NMR (CDCl$_3$): δ=3.22 (3H, s, —OCH$_3$), 3.50–3.91 (7H, m, H$_{3'}$, H$_{1''}$, H$_{2''}$, —OH), 4.10–4.32 (1H, m, H$_{2'}$), 4.38–4.52 (2H, m, H$_{1'}$), 8.43 (1H, s, H$_5$).

To 1.1 g (4.5 mmol) of 1-[2'-hydroxy-3'-(2''-methoxyethoxy)-propyl]-3-nitro-1,2,4-triazole, 10 ml of 1,4-dioxane was added and then 1.0 g (6.2 mmol) of DAST was dropwise added. Then, the mixture was reacted for a day at room temperature with stirring. After the reaction, to the reaction solution, 2 ml of water was added to decompose excess DAST. The solution was concentrated and partitioned between chloroform and water. The chloroform phase was washed with water, dried on magnesium sulfate and filtered. The filtrate was concentrated and subjected to isolation and purification by silica gel column chromatography to give 500 mg of 1-[2'-fluoro-3'-(2''-methoxyethoxy)-propyl]-3-nitro-1,2,4-triazole.

$^1$H-NMR (CDCl$_3$): δ=3.42 (3H, s, —OCH$_3$), 3.49–3.92 (6H, m, H$_{3'}$, H$_{1''}$, H$_{2''}$), 4.48–4.90 (2H, m, H$_{1'}$), 5.60 (1H, dm, —H$_{2'}$, J$_{H2-F}$=45 Hz), 8.42 (3H, s, H$_5$).

$^{19}$F-NMR (CDCl$_3$; standard: TFA): 113.00.

PREPARATION EXAMPLE 39

NT—CH₂CHFCH₂OCH₂CH——CH₂  (64)
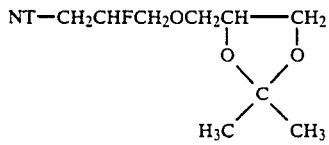

To a solution of 6.0 g (50 mmol) of 1,2-O-isopropylideneglycerol and 18.5 g (0.2 mmol) of epichlorohydrin in 50 ml of dioxane, 2.8 g (50 mmol) of potassium hydroxide was added and reacted for 3 hours at 70° C. After the reaction, the reaction mixture was filtered and the filtrate was concentrated to give 6.9 g of 3-(2,3-epoxypropyl)-1,2-O-isopropylideneglycerol.

A solution of 2.3 g (11 mmol) of 3-(2,3-epoxypropyl)-1,2-O-isopropylideneglycerol and 1.8 g (16 mmol) of 3-nitro-1,2,4-triazole in 5 ml of dioxane was reacted for 3 hours at 90° C. Then, the solution was concentrated and partitioned between chloroform and water. The chloroform phase was dried on magnesium sulfate and filtered. The filtrate was concentrated and subjected to isolation and purification by silica gel column chromatography to give 1.5 g of 1-(2'-hydroxy-4'-oxo-6',7'-isopropylidenedioxyheptyl)-3-nitro-1,2,4-triazole.

$^1$H-NMR (CDCl₃): δ=1.38 (3H, s, —OCH₃), 1.42 (3H, s, —CH₃), 3.40–3.83 (5H, m, H₃', H₅', —OH), 3.70 (1H, dd, H₇'$_a$, J$_{H7'b}$=8 Hz, J$_H'$=6 Hz), 4.80 (1H, dd, H₇'$_b$, J$_{H7'a}$=8 Hz, J$_{H6'}$=7 Hz), 4.18–4.60 (4H, m, H₁', H₂', H₆'), 8.39 (1H, s, H₅).

To 1.0 g (3.4 mmol) of 1-(2'-hydroxy-4'-oxo-6',7'-isopropylidenedioxyheptyl)-3-nitro-1,2,4-triazole, 10 ml of 1,4-dioxane was added and then 1.0 g (6.2 mmol) of DAST was dropwise added. Then, the mixture was reacted for a day at room temperature with stirring. After the reaction, to the reaction solution, 2 ml of water was added to decompose excess DAST. The solution was concentrated and partitioned between ethyl acetate and water. The ethyl acetate phase was washed with water, dried on magnesium sulfate and filtered. The filtrate was concentrated and subjected to isolation and purification by silica gel column chromatography to give 400 mg of 1-(2'-fluoro-4'-oxo-6',7'-isopropylidenedioxyheptyl)-3-nitro-1,2,4-triazole.

$^1$H-NMR (CDCl₃): δ=1.32 (3H, s, —CH₃), 1.39 (3H, s, —CH₃), 3.44–4.06 (6H, m, H₃', H₅', H₇'), 4.08–4.40 (1H, m, H₆'), 4.42–4.85 (2H, m, H₁'), 6.00 (1H, dm, H₂', J$_{HF}$=48 Hz), 8.34 (1H, s, H₅).

$^{19}$F-NMR (CDCl₃; standard: TFA): 113.0.

PREPARATION EXAMPLE 40

NT—CH₂CHFCH₂OCH₂CHCH₂OH  (65)
|
OH

To 1.0 g (3.4 mmol) of 1-(2'-fluoro-4'-oxo-6',7'-isopropylidenedioxyheptyl)-3-nitro-1,2,4-triazole, 50 ml of 2N—HCl was added and reacted for 6 hours at 80° C. Then, the reaction solution was partitioned by the addition of 100 ml of ethyl acetate. The ethyl acetate phase was washed with saturated sodium hydrogen carbonate solution and with saturated sodium chloride solution, dried on magnesium sulfate and filtered. The filtrate was concentrated and subjected to isolation and purification by silica gel column chromatography to give 300 mg of 1-(2'-fluoro-4'-oxo-6',7'-dihydroxyheptyl)-3-nitro-1,2,4-triazole.

$^1$H-NMR (CDCl₃): δ=3.42–4.05 (8H, m, H₃', H₅', H₇', —OH, —OH), 4.05–4.42 (1H, m, H₆'), 4.44–4.81 (2H, m, H₁'), 6.01 (1H, dm, H₂', J$_{HF}$=48 Hz), 8.31 (1H, s, H₅).

$^{19}$F-NMR (CDCl₃; standard: TFA): 113.1.

PREPARATION EXAMPLE 41

NI-CH₂CF₂COOCH₃  (1")

To 1.0 g (8.8 mmol) of 2-nitroimidazole and 2.0 g (19 mmol) of sodium carbonate, 20 ml of methanol was added. To the obtained mixture, 1.8 g (14 mmol) of tetrafluorooxetane was dropwise added. After stirring for 30 minutes at room temperature, the mixture was concentrated and partitioned between ethyl acetate and water. The ethyl acetate phase was dried on magnesium sulfate and filtered. The filtrate was concentrated and subjected to isolation and purification by silica gel column chromatography to give 1.48 g of methyl 3-(2'-nitroimidazol-1'-yl)-2,2-difluoropropionate as an oil.

$^1$H-NMR (CDCl₃): δ=3.89 (3H, s, —OCH₃), 5.26 (2H, t, —NCH₂, J$_{HF}$32 14 Hz), 7.21 (2H, s, H₄', H₅').

$^{19}$F-NMR (standard: TFA): 30.9.

PREPARATION EXAMPLE 42

NI-CH₂CF₂CONHCH₂CH₂OCH₃  (2")

To a solution of 1.74 g (7.40 mmol) of methyl 3-(2'-nitroimidazol-1'-yl)-2,2-difluoropronionate in 5.0 ml of dioxane, 2.0 ml (23 mmol) of 2-methoxyethylamine was dropwise added and stirred at room temperature for 1 hour.

After reaction, the solution was concentrated and subjected to isolation and purification by silica gel column chromatography to give 1.75 g of 3-(2'-nitroimidazol-1'-yl)-2,2-difluoropropionic acid methoxyethylamide as an oil. $^1$H-NMR (CDCl₃): δ=3.36 (3H, s, —CH₃), 3.45–3.58 (4H, m, —CH₂—O—), 5.22 (2H, t, H₁', J$_{HF}$=14 Hz), 6.94 (1H, bs, —CONH—), 7.18–7.27 (2H, m, H₄, H₅).

$^{19}$F-NMR (CDCl₃; standard: TFA): 32.0.

PREPARATION EXAMPLE 43

NI-CH₂CF₂CONHCH₂CH₂OH  (3")

To a solution of 1.49 g (6.34 mmol) of methyl 3-(2'-nitroimidazol-1'-yl)-2,2-difluoropronionate in 4.0 ml of methanol, 2.0 ml (33 mmol) of ethanolamine was added. After the same treatment as Preparation Example 42, 670 mg of 3-(2'-nitroimidazol-1'-yl)-2,2-difluoropronionic acid hydroxyethylamide was obtained as an oil.

$^1$H-NMR (CDCl₃): δ=3.39–3.62 (2H, m, —NHCH₂—), 3.67–3.88 (2H, m, —CH₂—O), 5.22 (2H, t, H₃, J$_{HF}$=14 Hz), 6.94 (1H, bs, —CONH—), 7.21 (2H, s, H₄', H₅').

$^{19}$F-NMR (CDCl₃; standard: TFA): 31.9.

PREPARATION EXAMPLE 44

NI-CH₂CHFCH₂OCH₃  (7")

To a solution of 914 mg (4.54 mmol) of 1-(2'-hydroxy-3'-methoxypropyl)-2-nitroimidazole in 5.0 ml of dry dioxane, 1.00 g (6.20 mmol) of DAST was dropwise added with cooling by ice and then reacted for 2 hours at room temperature with stirring. After reaction, to the solution, 5.0 ml of ethanol was added to decompose excess DAST. The solution was then concentrated and subjected to isolation and purification by silica gel column chromatography to give 480 mg of 1-(2'-'fluoro-3'-methoxypropyl)-2-nitroimidazole.

m.p. 39.0°–44.0° C.

$^1$H-NMR (CDCl$_3$): δ=3.44 (3H, s, —OCH$_3$), 3.58 (1H, dd, H$_{3'a}$, J$_{H3'a-H2'}$=3 Hz, J$_{H3'a-F}$=3 Hz), 3.80 (1H, d, H$_{3'b}$, J$_{H3'b-F}$=3 Hz), 4.32–4.56 (1H, m, H$_{1'a}$), 4.65–4.72 (1H, m, H$_{1'b}$).

$^{19}$F-NMR (CDCl$_3$; standard: TFA): 113.6.

PREPARATION EXAMPLE 45

NI-CH$_2$CHFCH$_2$OCOCH$_3$ (8')

To a solution of 3.93 g (17.1 mmol) of 1-(2'-hydroxy-3'-acetoxypropyl)-2-nitroimidazole in 30 ml of dry dioxane, 4.00 g of DAST was dropwise added with stirring and cooling by ice. After addition, the mixture was reacted for 5 hours at room temperature with stirring. Thereafter, to the solution, 10 ml of ethanol was added to decompose excess DAST. The solution was then concentrated and partitioned between chloroform and an aqueous solution of sodium hydrogen carbonate. The chloroform phase was dried on magnesium sulfate and filtered. The filtrate was concentrated and subjected to isolation and purification by silica gel column chromatography to give 1.15 g of 1-(2'-fluoro-3'-acetoxypropyl)-2-nitroimidazole.

$^1$H-NMR (CDCl$_3$): δ=2.15 (3H, s, —COCH$_3$), 4.12–5.18 (4H, m, H$_{1'}$, $_{H3'}$), 5.05 (1H, dm, H$_{2'}$, J$_{H2'-F}$=48.0 Hz), 7.19–7.26 (2H, m, H$_4$, H$_5$).

$^{19}$F-NMR (CDCl$_3$; standard: TFA): 113.6.

PREPARATION EXAMPLE 46

NI-CH$_2$CHFCH$_2$OH (9')

To 910 mg (3.94 mmol) of 1-(2'-fluoro-3'-acetoxypropyl)-2-nitroimidazole, 6N-HCl was added and stirred overnight at room temperature. The reaction mixture was concentrate and subjected to isolation and purification by silica gel column chromatography to give 280 mg of 1-(2'-fluoro-3'-hydroxypropyl)-2-nitroimidazole.

m.p. 84.0°–89.0° C.

$^1$H-NMR (CDCl$_3$+DMSO-d$_6$): δ=3.48–3.97 (2H, m H$_{3'}$), 4.52–5.24 (3H, m, H$_{1'}$, H$_{2'}$), 7.19 (1H, s, H$_5$), 7.42 (1H, s, H$_4$).

$^{19}$F-NMR (CDCl$_3$+DMSO-d$_6$; standard: TFA): 114.5.

PREPARATION EXAMPLE 47

NI-CH$_2$CF$_2$CH$_2$OH (25')

To a solution of 4.00 g (15.1 mmol) of 3-(2'-nitroimidazol-1'-yl)-2,2-difluoropropionic acid in 50 ml of dry THF (tetrahydrofuran) cooled to −40° C., 1.20 g (30.4 mmol) of NaBH$_4$ was gradually added in a nitrogen stream and then 7.6 ml (60 mmol) of BF$_3$O(C$_2$H$_5$)$_2$ was gradually added. After addition, the reaction mixture was stirred for one hour while cooling by ice, neutralized with dilute hydrochloric acid and extracted with ethyl acetate. The extract was dried on magnesium sulfate and filtered. The filtrate was concentrated and subjected to isolation and purification by silica gel column chromatography to give 510 mg of 1-(2',2'-difluoro-3'-hydroxypropyl)-2-nitroimidazole. $^1$H-NMR (CDCl$_3$): δ=3.88 (2H, t, H$_{3'}$, J$_{H3'-F}$=12 Hz), 5.08 (1H, t, H$_{1'}$, J$_{H1'-F}$=12 Hz), 7.22–7.30 (2H, m, H$_4$, H$_5$).

$^{19}$F-NMR (CDCl$_3$; standard: TFA): 33.5.

PREPARATION EXAMPLE 48

NI-CH$_2$CF$_2$CONHOH (44')

To a solution of 3.0 g (12.8 mmol) of methyl 3-(2'-nitroimidazol-1'-yl)-2,2-difluoropropionate in 30 ml of methanol, 1.0 (18.7 mmol) of hydroxyamine.hydrochloride was suspended. To the suspension, a solution of 1.0 g of potassium hydroxide in 20 ml of methanol was gradually dropwise added followed by reaction for 3 hours at room temperature.

The precipitate was filtrated off. The filtrate was concentrated and subjected to isolation and purification by silica gel column chromatography to give 160 mg of 3-(2'-nitroimidazol-1'-yl)-2,2-difluoropropionylhydroxyamide.

$^1$H-NMR (CD$_3$OD): δ=5.32 (2H, t, H$_3$, J$_{H3-F}$=15 Hz), 7.22 (1H, m, H$_5$), 7.52 (1H, s, H$_4$).

$^{19}$F-NMR (CD$_3$OD; standard: TFA): 34.5.

PREPARATION EXAMPLE 49

NI-CH$_2$CF$_2$CONHCH$_2$CH(OH)CH$_3$ (60')

To a solution of 1.0 g of methyl 3-(2'-nitroimidazol-1'-yl)-2,2-difluoropronipnate in 30 ml of dioxane, 1,0 g of 2-hydroxypropylamine was added and reacted at room temperature for 3 hours. Then, the reaction mixture was concentrated and subjected to isolation and purification by silica gel chromatography to give 530 mg of 3-(2'-nitroimidazol-1'-yl)-2,2-difluoropropionyl-(2''-hydroxypropyl)amide.

$^1$H-NMR (DMSO-d$_6$; standard: TMS): δ=1.09 3H, d, —CH$_3$, J$_{H2''-H3''}$=5 Hz), 3.16 (2H, t, —NCH$_3$, J$_{H1''-H2''}$=J$_{H1''-NH}$=6 Hz), 3.80 (1H, m, CH—O—), 4.88 (1H, d, —OH, J$_{H2''-OH}$=5 Hz), 5.36 (2H, t, CH$_2$CF$_2$, J$_{H1-F}$=15 Hz), 7.38 (1H, d, H$_{5'}$, J=1 Hz), 7.78 (1H, s, H$_{4'}$), 9.04 (1H, t, NH, J$_{HNH-H1''}$=4 Hz).

$^{19}$F-NMR (DMSO-d$_6$; standard: TFA): 31.0.

PREPARATION EXAMPLE 50

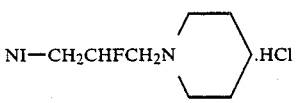
(69')

To a solution of 2.2 g (8.65 mmol) of 1-(2'-hydroxy-3'-piperidylpropyl)-2-nitroimidazole in 20 ml of dry dioxane, 2.5 g (15.5 mmol) of DAST was dropwise added with cooling by ice and reacted for 5 hours at room temperature. After reaction, to the solution, 10 ml of methanol was added to decompose excess DAST. Then, the solution was concentrated and partitioned between chloroform and water. The pH of the aqueous phase was adjusted to 12 by the addition of an aqueous solution of sodium hydroxide and the liquid was again partitioned between chloroform and water. The chloroform phase was dried on magnesium sulfate and filtered. The filtrate was concentrated and subjected to isolation and purification by silica gel chromatography to give 1-(2'-fluoro-3'-piperidylpropyl)-2-nitroimidazole, which was treated with hydrochloric acid to form a hydrochloride and crystallized from ethanol to give 560 mg of crystalline hydrochloride of 1-(2'-fluoro-3'-piperidylpropyl)-2-nitroimidazole.

$^1$H-NMR (DMSO-d$_6$): δ=1.22–2.18 (6H, m, piperidyl), 2.88–3.65 (4H, m, piperidyl), 3.50–3.98 (2H, m, H$_{3'}$), 4.72–4.88 (1H, m, H$_{1'a}$), 5.00–5.13 (1H, m, H$_{1'b}$), 5.76 (1H, dm, H$_{2'}$, J$_{H2'-F}$=51 Hz), 7.38 (1H, d, H$_5$, J$_{H5-H4}$=1.0 Hz), 78.6 (1H, d, H$_4$, J$_{H4-H5}$=1.0 Hz).

$^{19}$F-NMR (DMSO-d$_6$; standard: TFA): 106.1.

EXAMPLES 3 and 4

In the same manners as in Examples 1 and 2, values of ER in vitro and ER in vivo for the compounds (1'), (2') and (3') along with the comparative compounds (a), (b) and Misonidazole were determined. The results are shown in Table 3.

TABLE 3

| Compound | R$_f$(NI-R$_f$) | ER in vitro (mM) | ER in vivo (mg/kg) | LD$_{50}$ (g/kg) |
|---|---|---|---|---|
| (1') | —CH$_2$CF$_2$COOCH$_3$ | 1.40 (1.0) | — | — |
| (2') | —CH$_2$CF$_2$CONH(CH$_2$)$_2$OCH$_3$ | 1.61 (1.0) | 1.30 (100) | — |
| (3') | —CH$_2$CF$_2$CONH(CH$_2$)$_2$OH | 1.74 (1.0) | 1.58 (100) | — |
| Comparative (a) | —CH$_2$CHCl\|OH | — | 1.50 (200) | — |
| Comparative (b) | —CH$_2$CHCH$_2$F\|OH | — | 1.50 (200)<br>1.78 (200) | — |
| Comparative (Misonidazole) | —CH$_2$CHCH$_2$OCH$_3$\|OH | — | 1.40 (100)<br>1.58 (200) | 1.5 |

What is claimed is:

1. A nitroazole derivative of the formula:

$$NA-R_f \quad (I)$$

wherein NA represents 3-nitro-1,2,4-triazol-1-yl of the formula:

$$\text{(II)}$$

and R$_f$ is a fluorine-containing organic group $$-(CH_2)_n-\underset{\underset{Y}{|}}{\overset{\overset{X}{|}}{C}}-Z \quad (IV)$$

wherein X is a hydrogen atom or a fluorine atom; Y is a fluorine atom, a chlorine atom, a trifluoromethyl group, a methyl group or a hydroxy group, or X and Y together represent =O; Z is a hydrogen atom, a fluorine atom, a C$_1$-C$_5$ alkyl or a C$_1$-C$_5$ fluoroalkyl group which may be substituted with hydroxy, a group of the formula:

$$-(CHE)_m-CO-OR_1 \quad (V)$$

wherein R$_1$ is a hydrogen atom or a C$_1$-C$_5$ alkyl or a C$_1$-C$_5$ fluoroalkyl group, E is a hydrogen atom or a fluorine atom and m is 0 or 1, $$-CO-R_2 \quad (VI)$$

wherein R$_2$ is a C$_1$-C$_5$ alkyl or a C$_1$-C$_5$ fluoroalkyl group, $$-(CHE)_m-CO-N\underset{R_4}{\overset{R_3}{\diagup}} \quad (VII)$$

wherein R$_3$ and R$_4$ are the same or different and a hydrogen atom, a hydroxy group or a C$_1$-C$_5$ alkyl or a C$_1$-C$_5$ fluoralkyl group which may be substituted with a hydroxy group, a C$_1$-C$_5$ alkoxy group or an amide group, or R$_3$ and R$_4$ forms a 3 to 6 membered ring together with the nitrogen atom to which they bond, and E and m are the same as defined above, $$-(CHE)_m-N\underset{R_4}{\overset{R_3}{\diagup}} \quad (VIII)-(1)$$

wherein R$_3$, R$_4$, E and m are the same as defined above, $$-(CHE)_m-N\underset{\underset{O}{\overset{\|}{C}}-R_4}{\overset{R_3}{\diagup}} \quad (VIII)-(2)$$

wherein R$_3$, R$_4$, E and m are the same as defined above, $$-(CHE)_m-N\underset{\underset{O}{\overset{\|}{C}}-R_4}{\overset{\overset{O}{\overset{\|}{C}}-R_3}{\diagup}} \quad (VIII)-(3)$$

wherein R$_3$, R$_4$, E and m are the same as defined above, $$-(CHE)_m-A-R_5 \quad (IX)$$

wherein A is an oxygen atom or a sulfur atom, R$_5$ is a hydrogen atom, a C$_1$-C$_5$ alkyl or a C$_1$-C$_5$ fluoroalkyl group which may be substituted with a hydroxy group, a C$_1$-C$_5$ alkoxy group or a C$_1$-C$_5$ oxyacyl group, a group of the formula: —CO—R$_6$ in which R$_6$ is a C$_1$-C$_5$ alkyl group,

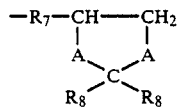 (X)
wherein $R_7$ is a $C_1$-$C_7$ alkylene group, $R_8$ is a $C_1$-$C_3$ alkyl group and A is the same as defined above, or
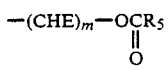 (XI)
wherein $R_5$ is a $C_1$-$C_5$ alkyl or a $C_1$-$C_5$ fluoroalkyl group and E and m are the same as defined above, Y and Z may together form $=CF-CF_3$ or $=CHOR_6$ in which $R_6$ is the same as defined above, and n is 0 or 1.
* * * * *